United States Patent [19]
Bender

[11] Patent Number: 4,745,911
[45] Date of Patent: May 24, 1988

[54] SUPPORT DEVICE FOR WEIGHTLIFTING

[76] Inventor: Mark R. Bender, 155 Cedar St., Ashland, Wis. 54806

[21] Appl. No.: 893,878

[22] Filed: Aug. 6, 1986

[51] Int. Cl.$^4$ .............................................. A61F 5/02
[52] U.S. Cl. ...................................................... 128/78
[58] Field of Search ......................... 2/338, 339, 312; 128/78; 272/123; 273/DIG. 11, 30, 189 A

[56] References Cited

U.S. PATENT DOCUMENTS

| 437,822 | 10/1890 | Reach | 2/338 |
|---|---|---|---|
| 732,289 | 4/1903 | Fischman | 2/338 |
| 1,258,052 | 3/1918 | Stall | 273/189 A |
| 1,584,753 | 10/1922 | York | 2/338 |
| 1,903,081 | 8/1931 | Wotherspoon | 2/338 |
| 2,596,884 | 5/1952 | Bailen | 2/338 |
| 2,906,260 | 9/1959 | Myers | 128/78 |
| 3,920,008 | 11/1975 | Lehman | 128/78 |
| 3,926,183 | 12/1975 | Spiro | 128/78 |
| 4,245,628 | 1/1981 | Eichley | 128/78 |
| 4,325,363 | 4/1982 | Berkeley | 128/78 |
| 4,348,774 | 9/1982 | Woodson | 2/338 |
| 4,545,370 | 10/1985 | Welsh | 128/78 |

FOREIGN PATENT DOCUMENTS 909970 11/1962 United Kingdom .................. 128/78
2030845 4/1980 United Kingdom .................. 2/338

Primary Examiner—Richard J. Apley
Assistant Examiner—James Prizant
Attorney, Agent, or Firm—Orrin M. Haugen; Thomas J. Nikolai; Frederick W. Niebuhr

[57] ABSTRACT

A weightlifting support belt is constructed of two layers of pliable material, fastened together with stitching along the layer peripheries. First and second straps, each with a D-shaped pull ring at its free end, extend longitudinally from opposite ends of a medial section of the belt. Transverse stitching lines divide the space between the layers into a series of transverse compartments spanning the width of the medial section. Flattened, helical coiled springs are contained in each compartment, acting as a flexure to stiffen the medial section while allowing localized torsional bending and arcuate flexing about axes running longitudinally of the medial section. Tape closure strips are provided on the straps for maintaining the straps in overlying relation to maintain the belt in a wrapping configuration about the lumbar region of an individual. An elastic cover strap, provided with a closure strip at its free end, overlies the outermost strap and D-shaped ring to maintain them against the inside strap.

18 Claims, 2 Drawing Sheets

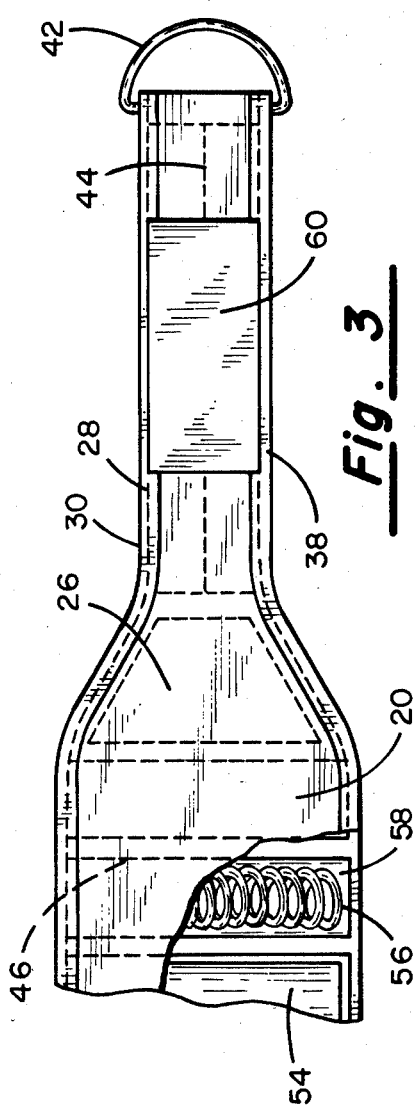
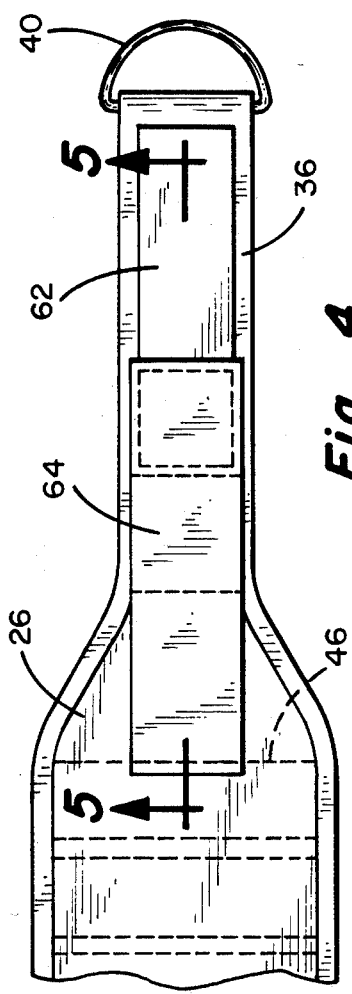
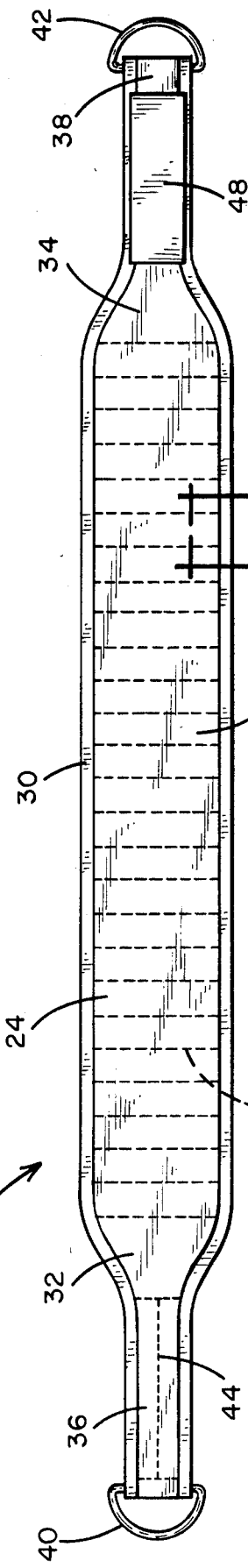
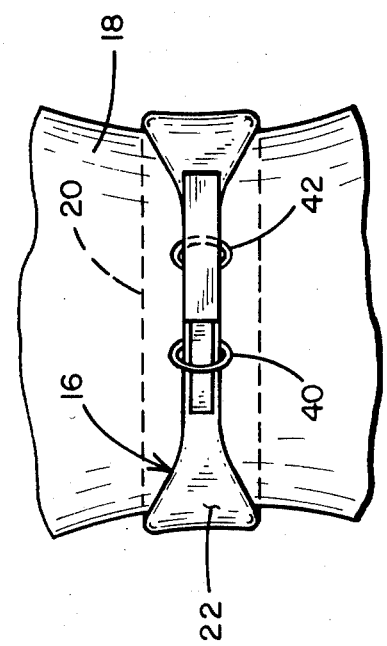

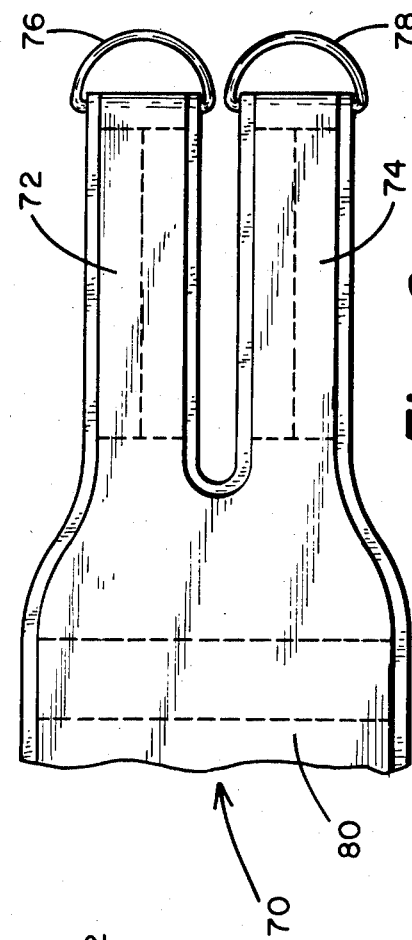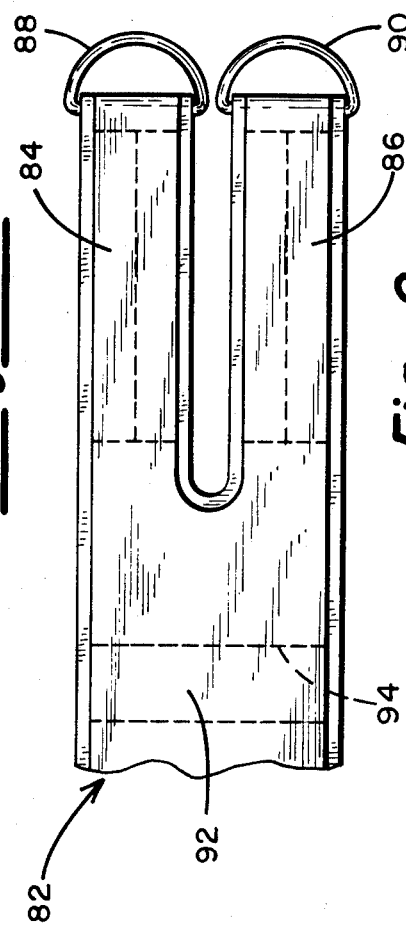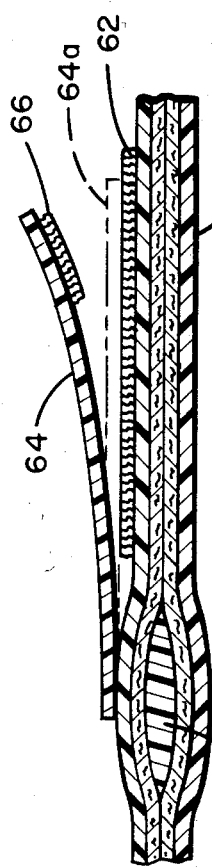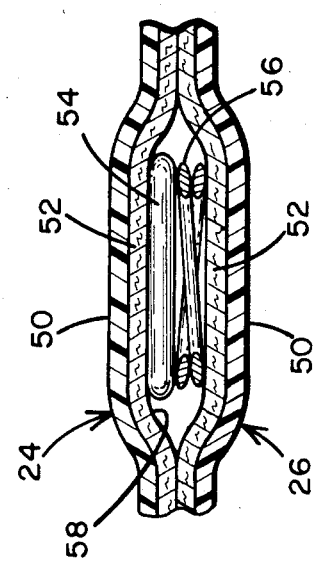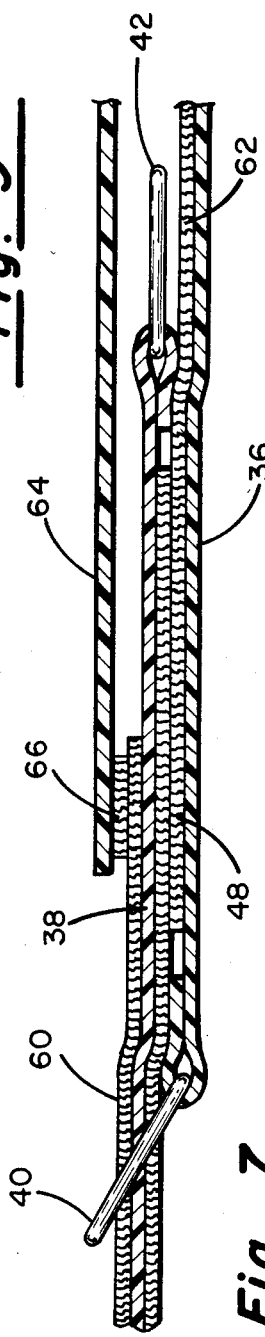

SUPPORT DEVICE FOR WEIGHTLIFTING

BACKGROUND OF THE INVENTION

This invention relates to support devices, more particularly to belts for supporting the lumbar region of the body when an individual is lifting weights.

The sport of weightlifting continues to grow in terms of the number participating. While initial public recognition tends to focus on the amount of weight lifted, particularly in international competition, the general increased concern for physical fitness has led to greater appreciation of the disciplined training, conditioning, agility and balance required of the weightlifter. One difficulty is that certain techniques in weightlifting can cause stress to the muscles throughout the lumbar region of the body, particularly the lower back muscles. Such stress occasionally causes severe injury, not only to the novice but to an experienced weightlifter attempting to exceed a prior lifted maximum weight.

To reduce the probability for injury, or to avoid reaggrevating an injury, a belt may be worn about the waist or lumbar region to support the muscle tissue. Typically constructed of leather, such belts support the stomach and lower back by holding them in, and assist the weightlifting effort by providing a surface for the stomach to push against. However, leather belts are flat, tend to bind, and do not conform to the shape of the body. This results in "gap" areas where the leather belt provides uneven, inadequate body support. Furthermore, a conventional belt buckle is inconvenient to adjust, does not provide infinite adjustment, and can pinch or otherwise irritate the skin.

Therefore it is an object of the present invention to provide a weightlifting belt that readily conforms to the lumbar region of the individual using the belt.

Another object is to provide a weightlifting belt which, when fastened about the body, provides substantially uniform support about the entire lumbar region.

Yet another object is to provide a means for conveniently fastening a weightlifting belt around the body, for adjusting its tightness if desired, while isolating such fastening means from any direct contact with the body.

SUMMARY OF THE INVENTION

To achieve these and other objects, there is provided a belt for supporting the lumbar region of an individual. The belt includes an elongate and pliable first layer, an elongate and pliable second layer shaped to conform to the first layer, and a joining means for connecting the first and second layers together about their peripheries to form a belt. The belt has a medial section, at least one first strap extended longitudinally from a first end of the medial section, and a second strap corresponding to each first strap and extended longitudinally from a second and opposite end of said medial section. A means is provided for segmenting the space between the first and second layers, at the medial section, into a series of transversely directed compartments spanning substantially the width of the medial section. A flexure means, deformable about a longitudinal axis, is contained within each compartment. A first connecting means is attached to the first layer along the first strap. A second connecting means is attached to the second layer along the second strap and positionable to releasably engage the first connecting means to maintain the second strap in overlying relation to the first strap, thereby to maintain the belt in a wrapping configuration about the lumbar region of an individual.

Preferably, the belt further includes an elastic cover strap attached to the first layer at the first end of the medial section and extended from the medial section parallel to the first strap. Then, a third connecting means is attached to the first layer along the second strap, and a fourth connecting means is attached to the free end of the cover strap. Upon elastic elongation of the cover strap, the fourth connecting means is positionable to releasably engage the third connector means to maintain the cover strap in overlying relation to the second strap.

A first ring can be mounted to the free end of the first strap, with a second, similarly sized D-shaped ring mounted to the second strap. The second ring and strap are inserted through the first ring in order to achieve the overlying relation on the first strap. This permits simultaneous pulling of the first and second rings, away from each other, in order to tighten the belt. Further, the connecting means can be strips of a closure tape, for example the nylon closure tape sold under the trademark VELCRO, to provide convenient and infinite adjustment of belt tightness.

The flexure means strengthens the belt in the radial direction to provide the necessary support, but flexes about longitudinal axes and can bend torsionally so that the belt readily conforms to the body. Thus the belt exerts substantially uniform force against the body over substantially all of its length.

IN THE DRAWINGS

The above and other features and advantages are more readily appreciated from consideration of the detailed description in light of the drawings, in which:

FIG. 1 is an elevational view of a weightlifting support belt constructed in accordance with the present invention and shown about the lumbar region of an individual;

FIG. 2 is a top plan view of the belt of FIG. 1;

FIG. 3 is a partial bottom view showing one end of the belt;

FIG. 4 is a partial bottom view showing the opposite end of the belt;

FIG. 5 is a sectional view taken along the line 5—5 of FIG. 4;

FIG. 6 is a sectional view taken along the line 6—6 of FIG. 2;

FIG. 7 is an end view showing the straps from opposite ends of the belt in belt-fastening engagement;

FIG. 8 is a partial top plan view of an alternative belt in accordance with the present invention; and FIG. 9 is a partial top plan view of another alternative embodiment of a belt in accordance with the present invention.

DETAILED DESCRIPTION OF THE PREFERRED EMBODIMENTS

Turning now to the drawings, there is shown in FIG. 1 a weightlifting support belt 16 in a wrapping configuration about a lower torso 18 of an individual, also referred to as the lumbar region of the body. Straps at opposite ends of the belt are shown fastened together in front of the body, at the abdominal region, while a medial section 20 of the belt, shown in broken lines, is centerd on the back and spans the distance across the lower back area. The outer surface 22 of the belt is slightly outwardly concave, to conform to the contour of lower torso 18. The structure for achieving this conformity is later explained.

FIG. 2 shows belt 16 in a flat configuration, following its removal from torso 18, in which it is an elongate structure with a shape essentially defined by a top layer 24 of a pliable material such as vinyl, and a bottom layer 26 (FIG. 4) having the same size and shape as the top layer and also of a pliable material. Layers 24 and 26 are aligned and joined together by edge stitching 28 (FIG. 3) through both layers and through an edge covering 30 folded over upon the peripheral edges of the layers.

Belt 16 thus is pliable and readily assumes either its wrapping or flat configuration. The configurations are related in that top layer 24 in FIG. 2 lies against torso 18 in FIG. 1, while the outer surface of FIG. 1 corresponds to bottom layer 26 shown in FIGS. 4 and 5.

As seen in FIG. 2, medial section 20 includes first and second tapered portions 32 and 34, which converge to first and second straps 36 and 38, respectively on opposite sides of the medial section, each strap extended longitudinally away from the medial section. The free end of first strap 36 is folded over upon itself to capture a first pull ring 40, which has a shape substantially like the letter "D". A second pull ring 42, substantially identical to the first ring in size and shape, is similarly mounted to the free end of second strap 38.

To reinforce and strengthen straps 36 and 38, internal stitching 44 is provided to secure, in contiguous relation, those portions of top and bottom layers 24 and 26 which form the straps. Further strength is provided by a series of spaced apart transverse stitching lines 46. Attached along the length of second strap 38 is a top closure strip 48, which preferably is a closure tape such as is available under the trademark VELCRO. The closure strip forms part of a connecting structure for belt 16 as is later explained.

From FIG. 6 it is seen that top and bottom layers 24 and 26 each consist of an outer sheet 50 of a plastic such as vinyl, and an inner fabric backing 52, which imparts structural stability and tensile strength to belt 16. A compressible liner 54 and an elongate flexure member 56 are contained in a compartment 58 between the top and bottom layers. Liner 54 cooperates with top layer 24 to isolate the body from the flexure member for greater comfort.

FIG. 3 shows that portion of the bottom of belt 16 which includes second strap 38, and reveals a first bottom closure strip 60 attached to strap 38. This figure further illustrates edge stitching 28 in addition to internal stitching 44 and transverse stitching lines 46.

A portion of bottom layer 24 is removed, to reveal that transverse stitching lines 46 the space between top and bottom layers 24 and 26, over the medial section, into a series of transverse compartments 58 spanning substantially the width of the medial section. Contained within each compartment 58 is a flexure member 56, preferably consisting of two flat interleaved helical coil springs. Each flexure member 56 permits arcuate bending of medial section 20 about axes running longitudinally of the belt, and further permits torsional bending about an axis running transversely, i.e. along the length of the flexure member. A properly dimensioned flat and rectangular leaf spring, while not illustrated, may serve as an alternative flexure member.

Together, flexure members 56, while tending to stiffen the otherwise pliant medial section 20, permit the medial section to bend about axes running longitudinally of the belt, and further allow very localized torsional bending. With belt 16 in the wrapping configuration, any "longitudinal" axis necessarily becomes a tangential axis, yet the nature of elastic bending remains the same. The result is a belt which can undergo highly localized bending and twisting if necessary, to conform to the body and provide uniform support and maximum comfort. The longitudinal distance between centers of adjacent compartments 58 is less than twice the compartment longitudinal dimension (i.e. width). This close spacing between compartments enhances the uniformity of support provided by flexure members 56.

Above each flexure member 56, or behind it as viewed in FIG. 3, is a compressible liner 54, the flexure having been removed from the bar left compartment in the figure to more clearly show the liner. So positioned, each of liners 54 lies between its associated flexure member 56 and lower torso 18, thus to increase comfort of the individual using belt 16.

FIG. 4 shows the opposite end of the belt to reveal a second bottom closure strip 62 attached to bottom layer 26 along the bottom of first strap 36. At the interior edge of first tapered portion 32, a cover strap 64 is attached to belt 16 by the most rightward one of transverse stitching lines 46. As seen from FIG. 5, such transverse stitching line provides a hinged connection for cover strap 64, permitting it to be pivoted or "peeled" away from first strap 36. A covering closure strip 66 is attached to cover strap 64 near its free end. The cover strap is constructed of an elastic material, and with belt 16 wrapped about torso 18, can be stretched to a length indicated by the broken lines at 64a. Also shown in FIG. 5 is a pad 68 of compressible material housed in the cavity between layers 24 and 26 along first tapered portion 32. A similar pad is housed between the layers at second tapered portion 34.

The front portion of belt 16, in the wrapping configuration, is shown in FIG. 7. To achieve this configuration, the belt first is wrapped loosely about the lumbar region of the body. Then, with cover strap 64 pivoted away from first strap 36, second ring 42 and second strap 38 are threaded through first ring 42 to place the second strap in overlying relation to the first strap. Acting in a manner well-known for closure tape, top closure strip 48 and second bottom closure strip 62 releasably engage to maintain the second strap in its overlying relation to the first strap. At this intermediate stage, particularly with cover strap 64 still pivoted away from the other straps, rings 40 and 42 may be gripped, one in each hand, and pulled away from one another to tighten belt 16 in the amount desired.

After tightening, and with closure strips 48 and 62 remaining engaged, cover strap 64 is stretched by hand a sufficient amount so that when it is pressed against the remainder of the belt, covering closure strip 66 lockingly engages first bottom closure strip 60. Due to its elasticity, cover strap 64 positively maintains strap 38 and ring 42 in place, to prevent the second ring from swinging free or catching upon anything, and to reinforce the overlapping engagement of straps 36 and 38 to securely fasten the belt.

Following use, cover strap 64 is simply lifted away, i.e. upwardly as viewed in FIG. 7, to disengage closure strips 60 and 66. Then, second ring 42 similarly is lifted away to disengage closure strips 48 and 62, and strap 38 and ring 42 are removed from first ring 40 to complete the unfastening of belt 16.

FIG. 8 shows one end of a second embodiment weightlifting support belt 70 in which is formed two first straps 72 and 74, each with a pull ring as indicated at 76 and 78. Belt 70 has two corresponding second straps, not shown.

While quite similar to belt 16, belt 70 has an enlarged medial section 80 approximately 50% wider than the medial section of belt 16. The widened medial portion is particularly well adapted for support of the lower back, and is a preferred modification for individuals using weightlifting as but one part of an overall body-building program. The first and second straps are provided in pairs of parallel straps, rather than individual straps, to increase flexibility and comfort of belt 70.

A third embodiment of weightlifting support belt 82 is shown in part in FIG. 9. Belt 82 includes a pair of first straps 84 and 86 having pull rings 88 and 90, respectively. A corresponding pair of second straps and rings are provided at the opposite end of belt 82. As is shown in connection with straps 84 and 86 but is also true for the corresponding second straps, the straps are attached directly to the portion of medial section 92 including transverse stitching lines 94, there being no tapered portion at either end of the medial section. Medial section 92 has a width uniform and approximately equal to the width of medial section 20. Belt 82 thus provides a uniform width around the body, a structure preferred for power lifters.

Thus, a belt constructed in accordance with the present invention readily conforms to the lumbar region of virtually any individual, due to the spaced apart flexure members which allow twisting as well as bending about longitudinal axes. An additional benefit from conformity with the body contours is that the belt gives uniform support around entire circumferential length of the body. The D-shaped rings and tape closure strips together provide a convenient means for initially fastening the belt and later adjusting it for tightness. The cover strap secures the connection between straps and prevents swinging or snagging of the ring, for added safety.

I claim:

1. A device for supporting the lumbar region of the body of an individual, comprising:

an elongate belt having a medial section including a pliable first layer, and a pliable second layer corresponding in size and shape to the first layer, said layers connected to one another by stitching along the peripheries thereof, and means comprising transverse stitching through said first and second layers for segmenting the space between said layers into a series of elongate, generally uniform and transverse compartments arranged substantially uniformly along substantially the length of said medial section, the longitudinal distance between centers of adjacent compartments being less than twice the compartment width; a plurality of elongate flexure members, each flexure member contained in one of said compartments and each compartment containing one flexure member, oriented transversely of said medial section and spanning substantially the width thereof, said flexure members having sufficient stiffness cooperating to provide a backing for said medial section while flexing to allow limited flexure of said medial section about axes running longitudinally thereof; said belt further including a first lapping means attached to a first end of said medial section and extended longitudinally therefrom; and a second lapping means attached to a second and opposite end of said medial section and extended longitudinally therefrom; a first connecting means mounted on said first lapping means; and a second connecting means mounted on said second lapping means and adapted to releasably engage said first connecting means to secure said belt in a wrapping configuration about the lumbar region of an individual, with said medial section positioned against the lower back of the individual and substantially centered thereon.

2. The device of claim 1 wherein:
said flexure means include a plurality of substantially flat, helically wound coils, each flexure means being contained in one of said compartments.

3. The device of claim 1 including:
a compressible lining contained in each of said compartments and along one side of an associated one of said flexure members contained in said compartment.

4. The device of claim 1 wherein:
said first lapping means comprises at least one elongate strap, and said second lapping means comprises a second elongate strap corresponding to each of said first straps.

5. The device of claim 4 wherein:
said first connecting means includes a first closure strip on one surface of said first strap, and said second connecting means includes a second closure strip on one surface of said second strap.

6. The device of claim 5 wherein:
said first lapping means further includes an elastic cover strap adapted for overlying contact against said second strap, and wherein said connecting means further includes a third closure strip on an opposite surface of said second strap, and a fourth closure strip at the free end of said cover strap and positionable, upon elastic elongation of said cover strap, to releasably engage said third closure strip and maintain said cover strap in overlying relation to said second strap.

7. The device of claim 6 further including:
a first ring attached to the free end of said first strap, and a second ring attached to the free end of said second strap, said second ring and second strap insertable through said first ring for overlying engagement with said first strap.

8. The device of claim 7 wherein:
said rings are substantially the same size and substantially D-shaped.

9. The device of claim 1 wherein:
said medial section further includes a first padded portion of said first end, and a second padded portion at said second end, with said first and second lapping means connected to said first and second padded portions, respectively.

10. The device of claim 9 wherein:
each of said padded portions converges in its width from said medial section to its associated lapping means.

11. The device of claim 6 wherein:
said first lapping means includes two first straps and two cover straps, and said second lapping means includes two second straps.

12. A belt for supporting the lumbar region of an individual, including:
an elongate and pliable first layer; an elongate and pliable second layer conforming to the size and shape of said first layer; and a joining means for connecting said first and second layers together about their peripheries to form a belt including a medial section, at least one first strap, extended longitudinally from a first end of said medial section, and a second strap corresponding to each first strap and extended longitudinally from a second and opposite end of said medial section; a means for segmenting the space between said first and second layers, at said medial section, into a series of elongate, generally uniform and transversely directed compartments substantially uniformly arranged along substantially the length of said belt at the medial section, the longitudinal separation between centers of adjacent compartments being less than two times the compartment width;

a flexure means comprising a plurality of substantially flat, helically wound coils contained within each of said compartments and deformable about a longitudinal axis; said flexure means having sufficient stiffness cooperating to provide a backing for said medial section while flexing to allow limited flexure of said medial section about axes running longitudinally thereof;

a first connecting means attached to said first layer along said first strap; and a second connecting means attached to said second layer along said second strap and positionable to releasably engage said first connecting means to maintain said second strap in overlying relation to said first strap and thereby maintain said belt in a wrapping configuration about the lumbar region of an individual.

13. The belt of claim 12 further including:

an elastic cover strap attached to said first layer at the first end of said medial section and extended from said medial section parallel to said first strap; a third connecting means attached to said first layer along said second strap; and a fourth connecting means attached to the free end of said cover strap and, upon elastic elongation of said cover strap, positionable to releasably engage said third connecting means to maintain said cover strap in overlying relation to said second strap.

14. The belt of claim 13 wherein:

said joining means includes stitching through said first and second layers at the peripheries thereof.

15. The belt of claim 13 wherein:

said segmenting means includes stitching through said first and second layers and in a series of substantially transverse lines across the width of said medial section.

16. The belt of claim 13 further including:

a first ring attached to the free end of each of said first straps, and a second ring attached to the free end of each of said second straps, each second ring and associated second strap insertable through its associated first ring for overlapping engagement with its associated first strap.

17. The belt of claim 16 wherein:

said first and second rings are substantially the same size and D-shaped to permit insertion of each ring through the other ring.

18. The belt of claim 13 further including:

a first pad between said first and second layers at the first end of said medial section, and a second pad between said layers at the second end of said medial section.

* * * * *